(12) United States Patent
Bradin

(10) Patent No.: US 8,148,579 B2
(45) Date of Patent: Apr. 3, 2012

(54) PRODUCTION OF GASOLINE FROM FERMENTABLE FEEDSTOCKS

(75) Inventor: David Bradin, Cary, NC (US)

(73) Assignee: CPS Biofuels, Inc., Raleigh, NC (US)

( * ) Notice: Subject to any disclaimer, the term of this patent is extended or adjusted under 35 U.S.C. 154(b) by 0 days.

(21) Appl. No.: 12/452,030

(22) PCT Filed: Jun. 12, 2008

(86) PCT No.: PCT/US2008/007368
§ 371 (c)(1),
(2), (4) Date: Dec. 10, 2009

(87) PCT Pub. No.: WO2008/156651
PCT Pub. Date: Dec. 24, 2008

(65) Prior Publication Data
US 2010/0137647 A1    Jun. 3, 2010

Related U.S. Application Data

(60) Provisional application No. 60/934,299, filed on Jun. 12, 2007.

(51) Int. Cl.
*C07C 45/00* (2006.01)
*C12P 7/00* (2006.01)

(52) U.S. Cl. ......... 568/387; 568/840; 435/148; 435/157

(58) Field of Classification Search ........... 568/382, 568/840
See application file for complete search history.

(56) References Cited

U.S. PATENT DOCUMENTS

| | | | |
|---|---|---|---|
| 4,311,854 A | 1/1982 | Weber et al. | |
| 5,096,883 A | 3/1992 | Mercer et al. | |
| 5,189,012 A | 2/1993 | Patel et al. | |
| 5,200,101 A | 4/1993 | Hsu et al. | |
| 5,695,606 A * | 12/1997 | Atalla | 162/79 |
| 5,898,023 A | 4/1999 | Francisco et al. | |
| 6,458,176 B2 * | 10/2002 | Yeh et al. | 44/437 |
| 6,858,048 B1 * | 2/2005 | Jimeson et al. | 44/452 |

FOREIGN PATENT DOCUMENTS

WO    WO/2007/027955    3/2007

OTHER PUBLICATIONS

Rosinski et al. Some aspects of the utilization of xylites. HCAPLUS, Accession No. 1967:423854; Document No. 67:52354. 1967.*
Zhu,Liu,Yang,Construction and characterizationof pta gene deleted mutant of Clostridium tyrobutyricm for enhanced butyric acid fermentation,(Biotech Bioeng),2005,pp. 154-166,V90.
Renz, Ketonization of Carboxylic Acids by Decarboxylation: Mechanism and Scope, European Journal of Organic Chemistry, vol. 2005, Issue 6, 979-988 (Jan. 25, 2005).

* cited by examiner

*Primary Examiner* — Sikarl Witherspoon
(74) *Attorney, Agent, or Firm* — Guerry L. Grune; ePatentmanager.com

(57) ABSTRACT

Methods are disclosed for forming heptan-4-one, and, optionally, heptan-4-ol, from fermentable sugars. The sugars are fermented using a bacteria or yeast that predominantly forms butyric acid. The butyric acid is subjected to catalytic ketonization conditions to form heptan-4-one, with concomitant loss of water and carbon dioxide. The heptan-4-one can be subjected to catalytic hydrogenation to form heptan-4-ol, an either of these can be included in gasoline compositions. In one aspect, the fermentable sugars are derived from lignocellulosic materials such as wood products, switchgrass, or agricultural wastes, which are delignified to form lignin, cellulose and hemicellulose. The cellulose and hemicellulose can be depolymerized to form glycose and xylose, either or both of which can be fermented by the bacteria. Thus, the methods described herein can convert biomass to a fuel composition or fuel additive, which can be used in a conventional gasoline engine, unlike traditional fuels such as ethanol or biodiesel.

14 Claims, No Drawings

PRODUCTION OF GASOLINE FROM FERMENTABLE FEEDSTOCKS

PRIORITY

The present application is a national-phase filing under 35 U.S.C. §371 of PCT International Application PCT/US2008/007368, titled "Production of Gasoline from Fermentable Feedstocks", filed 12 Jun. 2008, which claims priority under 35 U.S.C. §120 to U.S. Provisional Patent Application No. 60/934,299, titled "Production of Gasoline from Fermentable Feedstocks", filed 12 Jun. 2007.

FIELD OF THE INVENTION

The present invention relates to methods for producing a fuel product that can burn in a gasoline engine, from feedstocks containing, or which can be converted into, glucose, fructose, sucrose, and/or xylose. In particular, the invention relates to a method to ferment sugars to butyric acid, convert the butyric acid to heptan-4-one, and, add the heptan-4-one to conventional gasoline for use in gasoline engines.

BACKGROUND OF THE INVENTION

There are numerous efforts underway to generate renewable fuels from biomass ("biofuels"). One approach is to generate biodiesel fuel (predominantly fatty acid ethyl or methyl esters) from triglycerides. Another approach is to use the glycerol to form glycerol ethers, which can be added to biodiesel and/or diesel fuel. Still another approach is to convert cellulosic or starchy material to fermentable sugars, ferment the sugars to form alcohol, and add the alcohol to gasoline, such as E85 (an 85/15 ethanol/gasoline blend).

Each of these approaches is associated with certain limitations. To date, biomass has not been converted to hydrocarbons in the gasoline range, only biodiesel fuel, glycerol ethers, ethanol, and butanol. Since the majority of cars run on gasoline, this is a major limitation. Ethanol works fairly well as a gasoline additive, but the energy output in miles per gallon ("MPG") is far lower for gasoline/alcohol blends than for gasoline.

In addition, yeasts have a limited ability to use sugars other than glucose. Glucose is only one of the sugars available from starch hydrolysis or from the depolymerization of cellulose or hemicellulose. Agricultural wastes such as corn stover and rice straw, and biomass crops such as switch grass or poplar trees, and even waste newspaper can all be converted into ethanol. However, a major limitation of these processes is that these feedstocks also include large amounts of other sugars, such as xylose, which yeast cannot easily metabolize.

In order to maximize the yield from biomass, it would be advantageous to provide fermentation processes that use sugars other than glucose. In order to facilitate adoption of alternative fuels, it would be advantageous to provide alternative fuels and fuel additives that can be used in the world's existing energy infrastructure. The present invention provides such processes and alternative fuels and fuel additives.

SUMMARY OF THE INVENTION

In one aspect, the present invention relates to a process for converting biomass to heptan-4-one, and using the heptan-4-one as an alternative fuel or fuel additive.

Representative sugars that can be fermented include glucose, sucrose, fructose, and xylose. Starting from sugar, the process for producing heptan-4-one comprises two main steps. The first step is the fermentation of sugar to butyric acid or (butyrate ion), and the second step is the conversion of butyric acid to heptan-4-one, with loss of one molecule of water and one molecule of carbon dioxide, over a suitable catalyst. Optionally, the chemistry can be carried out on a conjugate base of butyric acid, such as calcium butyrate.

The sugars can be derived from carbohydrate hydrolysis, from cellulose and/or hemicellulose depolymerization, or other means for producing sugars. As such, the sugars can be derived from virtually any cellulosic or starchy material. Examples include sugar cane bagasse, wood pulp, sawdust and wood chips, recycled paper, switch grass, corn, corn husks and other plant materials. Many of these materials are lignocellulosic materials, which include a combination of lignin, cellulose and hemicellulose. Because xylose is inefficiently converted to ethanol, this process can be complementary to ethanol production. Xylose is a preferred feedstock.

There are several bacteria known to ferment monosaccharides to butyric acid, any of which can be used. The fermentation is typically performed under anaerobic conditions, since the bacteria/yeast are anaerobic in nature. One way to ensure that no aerobic fermentation occurs, such as that which would produce ethanol, is to bubble sulfur dioxide into the fermentation media. Examples of butyrate-producing bacteria include *Clostridium tyrobutyricum, Clostridium butyricum, Clostridium kluyveri, Clostridium pasteurianum, Fusobacterium nucleatum, Butyrivibrio fibrisolvens*, and *Eubacterium limosum*. Many of these also produce by-products, such as acetic acid, which lowers the overall yield. For this reason, it can be preferred to use bacteria which have been bred and/or genetically-modified to produce less or no acetic acid or other by-products than the wild-type bacteria.

Butyric acid, when subjected to the reaction conditions described herein for forming heptan-4-one, produces a product (heptan-4-one) which is immiscible with the fermentation broth, and can thus be easily separated. Alternatively, the butyric acid can be extracted from the fermentation broth, for example, using hexane as a solvent, and then reacted over a suitable catalyst to form the heptan-4-one. The heptan-4-one can be used as a solvent, as a fuel or fuel additive, which can be used directly in gasoline engines, or as a high-octane fuel additive.

The conversion of butyric acid to heptan-4-one is known in the art, and described, for example, in U.S. Pat. No. 4,311,854, the contents of which are hereby incorporated by reference.

Lignocellulosic materials include cellulose, hemicellulose, and a large amount of lignin. Cellulose is a glucose polymer, and hemicellulose is a glucose copolymer. These polymeric materials can be degraded, for example, using enzymatic degradation, to form fermentable monosaccharides. These saccharides primarily include glucose and xylose, either or both of which can be used to produce heptan-4-one. Lignin can be burned, and the energy from burning the lignin can fuel many of the operations, such as distillation, catalytic reforming, and isomerization, used in the processes described herein. Electricity can be generated from burning the lignin. The lignin can also be converted to syngas, and subjected to Fischer-Tropsch synthesis. The Fischer-Tropsch synthesis can be used to produce additional hydrocarbons suitable for use as feedstocks for making diesel or gasoline, as is known in the art.

In one embodiment, lignocellulosic materials are used to produce lignin, hemicellulose, and cellulose as separate fractions. There are several known methods for separating cellulose and hemicellulose from lignin, such as those used in the pulp and paper industry. Any of these can be used. The cellulose can be depolymerized to form glucose, and the hemicellulose can be depolymerized to form xylose. The glucose can be used in the process disclosed herein, or, alternatively, fermented to form ethanol, and the xylose can be used in the process described herein to form heptan-4-one. The lignin can be converted to syngas, and the syngas to other products, such as gasoline, diesel, or jet fuel.

Some species of algae are ideally suited to biodiesel production due to their high oil content (some well over 50% oil), and extremely fast growth rates. The carbon dioxide formed during the initial fermentation of sugars to butyric acid, and, optionally, the ketonization step, can be used to feed algae, where the algae generates triglycerides. Typically, a solvent such as heptan-4-one is used to extract the triglycerides from the algae. The heptan-4-one for this extraction can be derived from the process described herein. Thus, the process described herein for producing heptan-4-one is complementary to the process for producing triglycerides from algae, in that the feedstock for the growing algae and the extractant for the thus-formed triglycerides both can be derived from the process.

The process described herein also provides a source of hydrogen, derived from both the fermentation step. The hydrogen produced by the process can be used in fuel cells, in a Fischer-Tropsch reactor, as a fuel, or any other appropriate use for hydrogen. Gasoline, jet fuel, and diesel fuel derived from Fischer-Trospch synthesis are all well known to those of skill in the art. The carbon dioxide produced by the process can be trapped by algae, and used to produce triglycerides (which can be extracted using the heptan-4-one produced by the process described herein). The triglycerides can be used, for example, to produce biodiesel fuel. Thus, from lignocellulosic materials, products useful in gasoline, jet, and diesel engines can be produced, with much of the carbon dioxide that is formed being sequestered in the form of a fuel product.

There are numerous advantages of this process, over conventional processes for converting fermentable materials to ethanol. Whereas gasoline/alcohol blends provide fewer miles per gallon than gasoline, the instant process provides hydrocarbons in the gasoline range, from the same starting materials as those used to form ethanol, but which have higher energy per unit volume. The overall yield, when factoring in overall yield of products, and the BTU/unit volume of these products (i.e., ethanol and heptan-4-one), is similar to that obtained when forming ethanol.

DETAILED DESCRIPTION OF THE INVENTION

The present invention subjects sugars, such as those derived from biomass, waste wood pulp, wood chips, paper products, and other sources of fermentable sugars, to anaerobic fermentation conditions that favor butyric acid and/or isobutyric acid synthesis. The butyric acid can then be catalytically reacted, with cleavage of carbon dioxide and water, to form heptan-4-one, which can be reduced, if desired, to heptan-4-ol, and either of these products (heptan-4-one and heptan-4-ol) can be used directly as gasoline, or as components of a gasoline composition.

Using the methods described herein, with the abundant sources of fermentable sugars, one can synthesize enough gasoline to replace a substantial portion of the amount consumed that is presently derived from crude oil. The methods for converting fermentable sugars to heptan-4-one and/or heptan-4-ol, gasoline, and/or components of gasoline are described in more detail below.

I. Sources of Fermentable Sugars

There are many sources of fermentable sugars. These include corn syrup, steepwater, sugar derived from beets and/or sugar cane, cellulosic materials and lignocellulosic materials. The lignocellulose materials include switchgrass, softwood pulps, hardwood pulps and non-wood plant pulps, for example, kenaf, flax, bagasse and rice plant pulps.

Cellulose, a glucose polymer, can be converted to glucose by using cellulose enzymes. Waste paper and delignified wood pulp can be used as cellulosic feedstocks for this conversion.

Lignocellosic materials, on the other hand, must first be delignified. Delignification methods are well known to those of skill in the art, and include the use of various enzymes, such as xylanases, and oxidizing agents such as ozone, oxygen, hydrogen peroxide, chlorine, and chlorine dioxide. Wood pulp that has been subjected to delignification is often referred to as "chemical pulp." Representative chemical pulps include Kraft pulps and soda pulps, which can be hardwood Kraft pulps or softwood Kraft pulps. The pulp is optionally digested, or digested and oxygen-bleached, before the enzyme treatment.

Representative enzymes for enzymatic delignification, and for hemicellulose depolymerization, include hemicellulases, such as xylanase, manganese peroxidase and laccase mediator systems. Numerous hemicellulases are commercially, any of which can be used. For example, hemicullulase-containing agents available in trade under the trademark of CALTAZYME, made by CLARIANT CO., ECOPULP, made by RHOM ENZYME FINLAND OY, or SUMIZYME, made by SHINNIHON CHEMICAL CO., and xylanase produced by microorganisms in genus *Tricoderma*, genus *Termomyces*, genus *Aureobasidium*, genus *Streptomyces*, genus *Aspergillus*, genus *Clostridium*, genus *Bacillus*, genus *Dermatoga*, genus *Thermoascus*, genus *Cardoceram* and genus *Thermomonospora*, can be employed. Such hemicellulase contributes to enhancing the bleaching efficiency in the enzyme treatment step by decomposing and removing the hemicellulose in the chemical pulp.

To form xylose from a chemical pulp, the pulp can be subjected to an enzyme treatment using hemicellulase, and after a permeation treatment using the separation membrane is completed, the resultant non-permeated fraction can be collected. In the non-permeated fraction, the xylooligosaccharide-lignin complex can be concentrated, and separated from the non-permeated fraction. A xylooligosaccharide can be isolated from a xylooligosaccharide-lignin complex by adjusting the pH value of the non-permeated fraction to 2 to 4 and heating the complex for an appropriate amount of time at an appropriate temperature. During the heating procedure, the xylooligosaccharide complex is converted into a mixture of mono- to decamers of xylose. The di- to decamers of xylose is recovered together with the remaining xylooligosaccharide from the heated non-permeated fraction. Further processing, for example, with hemicellulases, converts the di- to decamers of xylose to xylose, as is known in the art. The reaction mixture delivered from the enzyme treatment system can be filtered to recover the enzyme-treated pulp, and a filtrate containing various saccharides can be collected. In some processes, when a hardwood Kraft pulp is used, the filtrate contains substantially no glucose or arabinose, and xylose is obtained as close to 100% of the saccharides in the filtrate.

II. Selection of Bacteria for Fermenting the Sugars to Butyric Acid

Butyrate is produced as end product of a fermentation process solely performed by obligate anaerobic bacteria. Examples of butyrate producing species include *Clostridium* tyrobutyricum, *Clostridium butyricum*, *Clostridium kluyveri*,

*Clostridium pasteurianum, Fusobacterium nucleatum, Butyrivibrio fibrisolvens,* and *Eubacterium limosum.*

The pathway starts with the glycolytic cleavage of glucose to two molecules of pyruvate, as happens in most organisms. Pyruvate is then oxidized into acetyl coenzyme A using a unique mechanism that involves an enzyme system called pyruvate-ferredoxin oxidoreductase. Two molecules of carbon dioxide ($CO_2$) and two molecules of elemental hydrogen ($H_2$) are formed in the process and exit the cell.

Then, acetyl coenzyme A converts into acetoacetyl coenzyme A; the responsible enzyme is acetyl-CoA-acetyl transferase. Acetoacetyl coenzyme A converts into β-hydroxybutyryl CoA, and the responsible enzyme for this conversion is β-hydroxybutyryl-CoA dehydrogenase. β-hydroxybutyryl CoA converts into crotonyl CoA, and the responsible enzyme is crotonase.

Crotonyl CoA converts into butyryl CoA ($CH_3CH_2CH_2C=O-CoA$), and the responsible enzyme is butyryl CoA dehydrogenase.

A phosphate group replaces CoA to form butyryl phosphate; responsible enzyme: phosphobutyrylase.

The phosphate group joins ADP to form ATP and butyrate; responsible enzyme: butyrate kinase.

ATP is produced, as can be seen, in the last step of the fermentation. 3 ATPs are produced for each glucose molecule, a relatively high yield. The balanced equation for this fermentation is:

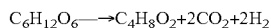

$$C_6H_{12}O_6 \rightarrow C_4H_8O_2 + 2CO_2 + 2H_2$$

There are several known strains of *Clostridium* bacteria which, under anaerobic conditions, convert glucose, fructose, and xylose to butyric acid, among other fermentation products. Acetic acid is one of the other products that are commonly produced.

Many clostridia are capable of forming butyric acid as an end product of their metabolism, which has a distinct rancid aroma and is often associated with this genus. Four nutritional groups of clostridia have been established based upon their preferred growth substrates: saccharolytic, proteolytic, saccharolytic and proteolytic and the so-called specialists. Saccharolytic clostridia use carbohydrates such as xylose, mannitol, glucose, fructose, lactose, or raffinose as their primary source of carbon and energy. Some saccharolytic species specialize in degrading polymers such as cellulose, chitin and pectin through the secretion of exoenzymes into the environment. Proteolytic species excrete proteases into the environment that degrade proteins to peptides and amino acids that are then transported inside the cell. The third group of clostridia can utilize both proteolytic and saccharolytic pathways for growth. The specialists are those clostridia that are restricted to degradation of just one or a few compounds. For example, *Clostridium acidiurici* grows on purines such as adenine or uridine, but not on sugars or amino acids, whereas *Clostridium cochlearium* can only use glutamate, glutamine, and histidine for growth. As a group, however, clostridia are capable of attacking a wide variety of substrates and play an important role in the degradation of organic compounds in many anaerobic environments

*Clostridium tyrobutyricum* is an anaerobe producing butyric acid, acetic acid, hydrogen and carbon dioxide. Researchers have engineered *Clostridium* bacteria which include mutations in various genes necessary to produce acetic acid, to maximize the yields of butyric acid. These genes include ack and pta, encoding enzymes AK and PTA, which are each involved in the acetate formation pathway. Gene knockout experiments were carried out in over-producing strains, and the results were published (*Biotechnol. Bioeng.* 90:154-166 (2005).

One example of a suitable genetically modified *Clostridium tyrobutyricum* is *Clostridium tyrobutyricum* ATCC 25755, an acidogenic bacterium, producing butyric acid, acetic acid, carbon dioxide and hydrogen as its main fermentation products. In these bacteria, genes in the acetic acid formation pathway in *C. tyrobutyricum* were disrupted, in order to enhance the production of butyrate and hydrogen. http://www.ct.ornl.gov/symposium/index_files/5abstracts/5_11.htm These researchers produced two mutants, phosphotransacetylase gene (pta) deleted mutant (PPTA-Em) and higher hydrogen-producing mutant (HydEm), which are capable of producing butyric acid and hydrogen from glucose and xylose, both of which are formed from lignocellulosic materials. Of these two, PPTA-Em produced a higher concentration (>50 g/L) of butyric acid with a higher yield (>50%) than those from the wild type *Clostridium tyrobutyricum*. Xylose is a preferred feedstock for these bacteria, producing significantly higher yields of butyric acid than glucose.

The ability to effectively minimize or shut off acetic acid production is an important component to the present invention. That is, butyric acid can be subjected to ketonization (and simultaneous decarboxylation) conditions, acetic acid can as well, yielding acetone. While the acetone is readily separated from the heptan-4-one, the yield of heptan-4-one is reduced. Accordingly, bacteria which predominantly form butyric acid (or butyrate) over acetic acid (or acetate) are preferred. Ideally, the bacteria form butyric acid predominantly over acetic acid (i.e., a ratio of butyric acid/acetic acid of at least 2:1, preferably 3:1, more preferably 4:1 or more).

III. Fermentation Conditions.

Ideally, the bacteria are restrained in immobilized cell bioreactors, such as fibrous-bed bioreactors (FBBs), to carry out the fermentation. However, any type of fermenter can be used. The use of immobilized cell bioreactors helps re-use the bacteria. The fermentation broth can be removed, while retaining the bacteria. The butyric acid in the fermentation broth can be extracted, with the extractant heated over a Lewis acid catalyst to yield 4-heptanone, or the fermentation broth can be heated, with the water driven off, although the former is preferred.

Continuous decantation, evaporative removal, or extraction of the butyric acid allows the fermentation medium to be continuously sterilized and minimizes water use. The non-stop nature of the fermentation process allows substrate concentrations to be constantly kept at optimal levels and therefore fermentation efficiency is maximized.

Improved varieties of yeast, produced through clonal selection techniques, can raise the tolerance levels of the yeast and/or bacteria to butyric acid concentrations, which will also improve efficiency. That said, currently known *Clostridium* variants can produce up to 50 g/liter of butyric acid, which is a fairly high tolerance level.

IV. Conversion of Butyric acid to Heptan-4-one

The butyric acid and/or isobutyric acid formed during the fermentation can be catalytically converted to heptan-4-one, with loss of carbon dioxide and water. Suitable catalysts and reaction conditions are known in the art (see, for example, U.S. Pat. No. 4,311,854). Some of these include heating the butyric acid at a temperature of from 300-525° C., depending on the catalyst, over a variety of Lewis acid catalysts, such as aluminum chloride, manganese dioxide, cerium oxide, lanthanum oxide, and the like.

Further, "dry distillation" of calcium butyrate can be performed at these temperatures, yielding 4-heptanone and calcium carbonate. The calcium butyrate can be produced, for example, by extracting the fermentation broth with a suitable solvent to obtain the butyric acid, extracting the solvent with calcium hydroxide to form the calcium butyrate, and, for example, evaporating off the water, or adding a co-solvent in which calcium butyrate is insoluble, to isolate calcium butyrate.

Additionally, calcium butyrate is one of the few compounds that exhibits "reverse solubility," in that it precipitates in hot water, but redissolves when placed in cold water. Thus, the fermentation broth can be treated with sufficient calcium hydroxide to form a solution of calcium butyrate, the solution can be heated to precipitate the calcium butyrate, the calcium butyrate can be isolated and converted to 4-heptanone, and the solution (minus the precipitated calcium butyrate) can be re-used as a fermentation broth. In this manner, the water usage is minimized, and carbon dioxide that would otherwise be off-gased is captured in the form of calcium carbonate, which itself can be used commercially. Precipitated calcium carbonate finds varied commercial uses, including the manufacture of paper, rubber, plastics, glass, textiles, putties, chalks, sealant, adhesives, paints, inks, varnishes, food, cosmetics, dentrifices, chemicals and pharmaceuticals.

A review of catalysts and conditions for performing the conversion is provided in Renz, Ketonization of Carboxylic Acids by Decarboxylation: Mechanism and Scope, *European Journal of Organic Chemistry*, Volume 2005, Issue 6, 979-988 (Jan. 25, 2005), the contents of which are hereby incorporated by reference.

One set of suitable conditions is as follows:
A quartz tube of 120 cm length and 28 mm inside diameter is filled with 300 ml of catalyst corresponding to a bed height of about 80 cm. The catalyst consists of 2% by weight of lanthanum in the form of di-lanthanum trioxide on alumina balls of the Pechiney A type (2 to 4 mm diameter). A layer of 30 cm of Raschig rings (4 mm diameter) functioning as evaporation zone is arranged above the catalyst. The tube is heated to a temperature of around 350° C., for example, in an electric furnace. An intense condenser terminating in a receiver with a drain valve can be connected at the lower outlet of the reactor. After a temperature of around 350° C. has been reached, n-butyric acid is introduced at the top of the reaction tube at a controlled rate. At the same time, the temperature is increased to 450° C. The butyric acid evaporates in the Raschig ring zone, and contacts the catalyst bed in gaseous form and is reacted, with cleavage of water and carbon dioxide, to form the corresponding ketone. After having emerged from the reactor, the vapor condenses in the intense condenser arranged downstream of the reactor. The resultant liquid product is collected in a receiver.

The reaction product is obtained at a rate of 75 ml per hour corresponding to a space velocity of 0.25. The organic phase and the aqueous phase are separated. The conversion is 92% and the selectivity (based on heptanone-4)>99%. The heptanone-4 is obtained in a purity of 99%.

These or other conditions can be scaled-up to produce heptan-4-one on a commercial scale.

The heptan-4-one has a boiling point of 145° C., a density of 0.817 g/ml at 20° C., is insoluble in water, but soluble in organic solvents, ethanol and ethers, and has GRAS (generally regarded as safe) status (FEMA GRAS No. 2546). Because the heptanone is GRAS, and can even be used as a flavoring in food products if desired, it offers a significant advantage over other fuel products, such as conventional gasoline, which is toxic if ingested.

If desired, the heptan-4-one can be converted to heptan-4-ol by catalytic hydrogenation. Although a variety of hydrogenation conditions are known, one set of conditions involves using a nickel catalyst containing 55% of Ni on kieselguhr. The heptan-4-one can be reduced in near quantitative yield within about 3 hours at about 150° C. and 100 bars of pressure.

V. Formation of a Fuel Additive or Fuel Product

The heptan-4-one and/or heptan-4-ol can be used alone, either as a solvent, a fuel, or a fuel additive, or can be combined with other desired gasoline components to form a gasoline composition. The gasoline composition can include various additives, such as lubricants, emulsifiers, wetting agents, densifiers, fluid-loss additives, corrosion inhibitors, oxidation inhibitors, friction modifiers, demulsifiers, anti-wear agents, anti-foaming agents, detergents, rust inhibitors and the like. Other hydrocarbons, such as those described in U.S. Pat. Nos. 5,096,883 and/or 5,189,012, may be blended with the fuel, provided that the final blend has the necessary octane values, pour, cloud and freeze points, kinematic viscosity, flash point, and toxicity properties.

Detergent additives are typically used in the concentration range of 50 ppm to 300 ppm. Examples of detergents and metal rust inhibitors include the metal salts of sulfonic acids, alkylphenols, sulfurized alkylphenols, alkyl salicylates, naphthenates and other oil soluble mono and dicarboxylic acids such as tetrapropyl succinic anhydride. Neutral or highly basic metal salts such as highly basic alkaline earth metal sulfonates (especially calcium and magnesium salts) are frequently used as such detergents. Also useful is nonylphenol sulfide. Similar materials made by reacting an alkylphenol with commercial sulfur dichloride. Suitable alkylphenol sulfides can also be prepared by reacting alkylphenols with elemental sulfur. Also suitable as detergents are neutral and basic salts of phenols, generally known as phenates, wherein the phenol is generally an alkyl substituted phenolic group, where the substituent is an aliphatic hydrocarbon group having about 4 to 400 carbon atoms.

Some organometallic compounds, for example, barium organometallics, act as combustion catalysts, and can be used as smoke suppressants. Adding these compounds to fuel can reduce the black smoke emissions that result from incomplete combustion. Smoke suppressants based on other metals, e.g., iron, cerium, or platinum can also be used.

Anti-foaming additives such as organosilicone compounds can be used, typically at concentrations of 10 ppm or less. Examples of anti-foaming agents include polysiloxanes such as silicone oil and polydimethyl siloxane; acrylate polymers are also suitable.

Antioxidants can be added to the fuel or fuel additive composition to neutralize or minimize degradation chemistry. Suitable antioxidants include, for example, hindered phenols and certain amines, such as phenylenediamine. They are typically used in the concentration range of 10 ppm to 80 ppm. Examples of antioxidants include those described in U.S. Pat. No. 5,200,101, which discloses certain amine/hindered phenol, acid anhydride and thiol ester-derived products.

Multi-component fuel stabilizer packages may contain a dispersant. Dispersants are typically used in the concentration range of 15 ppm to 100 ppm.

Examples of friction modifiers include fatty acid esters and amides, glycerol esters of dimerized fatty acids and succinate esters or metal salts thereof.

Examples of anti-wear agents include zinc dialkyldithiophosphate, zinc diary diphosphate, and sulfurized isobutylene. Additional additives are described in U.S. Pat. No. 5,898,023 to Francisco et al., the contents of which are hereby incorporated by reference.

VI. Methods for Converting Lignin to Hydrocarbons

As discussed above, the use of lignocellulosic materials provides, in addition to the fermentable sugars, a significant amount of lignin. The lignin can simply be burned, and the thermal energy used to provide energy for other steps described elsewhere herein. The lignin can also be converted to electric power, for example, when its heat energy is passed through a steam turbine to generate electricity.

The lignin can also be converted to synthesis gas, and the synthesis gas used to generate alcohols, such as methanol or ethanol, or hydrocarbons. The hydrocarbons can be converted, using known steps, to jet fuel, diesel fuel, and/or gasoline, among other products. The conversion to synthesis gas is typically carried out at high temperatures, often using "black liquor" resulting from the delignification of lignocellulosic materials. The black liquor includes inorganic pulping chemicals and lignin, among other substances. At high temperatures, a complex gas mixture including primarily carbon monoxide, hydrogen, carbon dioxide and methane is produced, and the inorganic chemicals can be isolated and reused, for example, in pulping operations. Because of its relatively high sulfur content, this gas mixture must be de-sulfurized before use in Fischer-Tropsch synthesis. Fischer-Tropsch synthesis is are well known to those of skill in the art, and thus not described in detail here.

VII. Methods for Converting Cellulose to Ethanol

In the production of cellulosic ethanol, cellulose is depolymerized to form glucose, which is then fermented to form ethanol. Enzymes and fermentation conditions for carrying out these steps are well known in the art, and need not be described in more detail here.

VIII. Combined Use of Components of Lignocellulosic Material to Produce Fuel

Using the process described herein, one can take a lignocellulosic material, and after conversion to each of the component parts, lignin, cellulose, and hemicellulose, can produce a variety of fuel products in the gasoline, jet, and diesel ranges. That is, as discussed herein, the hemicellulose can be depolymerized to form xylose, and the xylose converted to heptan-4-one and/or heptan-4-ol. The lignin can be converted, by Fischer-Tropsch synthesis, to hydrocarbons in the gasoline, jet and diesel range. The cellulose can be converted, for example, to ethanol. Finally, as discussed in more detail below, even the carbon dioxide formed during the fermentation and Fischer-Tropsch steps can be re-used to grow algae, which algae produce triglycerides (which can be used to form biodiesel, or, as described in PCT Wo 2007/027955, converted to a variety of products in the gasoline, jet, or diesel ranges by hydrolysis, thermal decarboxylation, and various downstream steps such as isomerization, hydrocracking, and hydrofinishing.

IX. Use of the Process in Combination with Algae to form Triglycerides/Biodiesel In a separate embodiment, the carbon dioxide produced during the fermentation and/or the ketonization steps can be used to grow algae, ideally strains of algae which produce relatively high volumes of triglycerides (i.e., greater than 30% by weight). The triglycerides can optionally be extracted using the heptan-4-one or heptan-4-one isomers produced using the process described herein.

X. Use of the Hydrogen Formed During the Fermentation Step

At least a portion of the hydrogen formed during the fermentation can be isolated, and used in hydrogenation reactions, fuel cells, Fischer-Tropsch synthesis, hydrocracking, or other such uses for hydrogen, as are known in the art.

All references cited herein are hereby incorporated by reference in their entirety, for all purposes. Modifications and variations of the present invention relating to a fuel additive composition and an alternative fuel derived from the composition will be obvious to those skilled in the art from the foregoing detailed description of the invention.

The invention claimed is:

1. A method for preparing heptan-4-one, comprising the steps of:
   a) subjecting an aqueous solution comprising glucose, xylose, and/or fructose to fermentation conditions using bacteria which produces, as a fermentation product, predominantly butyric acid,
   b) subjecting the butyric acid to suitable catalysis conditions to form heptan-4-one, with liberation of carbon dioxide and water, wherein the bacteria is a *Clostridium tyrobutyricum* genetically modified to reduce formation of acetic acid.

2. The method of claim 1, wherein the aqueous solution comprising glucose, xylose and/or fructose is obtained from a lignocellulosic material by steps comprising:
   a) delignification, and
   b) depolymerization of cellulose and/or hemicellulose.

3. The method of claim 1, wherein the source of the glucose, xylose, and/or fructose comprises corn syrup or other corn by-products.

4. The method of claim 1, wherein the source of the glucose, xylose, and/or fructose comprises switch grass or sugar cane bagasse.

5. The method of claim 1, wherein the source of the glucose, xylose, and/or fructose comprises wood, sawdust, wood chips, pulp, and/or paper.

6. The method of claim 1, wherein the source of the glucose, xylose, and/or fructose is derived from corn.

7. The method of claim 1, wherein the bacteria is *Clostridium tyrobulyricum* ATCC 25755.

8. The method of claim 1, wherein the heptan-4-one is further subjected to catalytic hydrogenation to form heptan-4-ol.

9. The method of claim 2, wherein lignin obtained from the lignocellulosic material is converted to synthesis gas.

10. The method of claim 9, wherein the synthesis gas is subjected to Fisher-Tropsch synthesis.

11. A method for preparing heptan-4-one, comprising the steps of:
   a) subjecting an aqueous solution comprising glucose, xylose, and/or fructose to fermentation conditions using a bacteria which produces, as a fermentation product, predominantly butyric acid,
   b) subjecting the butyric acid to suitable catalysis conditions to form heptan-4-one, with liberation of carbon dioxide and water, wherein the bacteria is genetically modified to reduce or eliminate formation of acetic acid wherein the carbon dioxide produced during the fermentation and/or ketonization steps is sequestered with algae.

12. The method of claim 11, wherein the algae produce triglycerides.

13. The method of claim 12, wherein the triglycerides are extracted from the algae using at least a portion of the (heptan-4-one produced in the process of claim 1.

14. A method for preparing heptan-4-one, comprising the steps of:
  a) subjecting an aqueous solution comprising xylose to fermentation conditions using bacteria which produces, as a fermentation product, predominantly butyric acid, and
  b) subjecting the butyric acid to suitable catalysis conditions to form heptan-4one, with liberation of carbon dioxide and water, wherein the bacteria is a *Clostridium tyrobutyricum* genetically modified to reduce formation of acetic acid.

* * * * *